United States Patent
Tets et al.

(10) Patent No.: US 11,135,253 B2
(45) Date of Patent: Oct. 5, 2021

(54) DRUGS (VARIANTS) AND METHODS FOR RESTORING MICROFLORA

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 266 days.

(21) Appl. No.: 15/780,909

(22) PCT Filed: Dec. 2, 2016

(86) PCT No.: PCT/RU2016/000845
§ 371 (c)(1),
(2) Date: Jun. 1, 2018

(87) PCT Pub. No.: WO2017/095269
PCT Pub. Date: Jun. 8, 2017

(65) Prior Publication Data
US 2019/0192583 A1    Jun. 27, 2019

(30) Foreign Application Priority Data

Dec. 4, 2015   (RU) ................ RU2015152096

(51) Int. Cl.
| | | |
|---|---|---|
| A61K 35/744 | (2015.01) | |
| A61K 35/66 | (2015.01) | |
| C12N 1/20 | (2006.01) | |
| A61P 1/00 | (2006.01) | |
| A61P 35/00 | (2006.01) | |
| A61K 9/00 | (2006.01) | |
| A61K 9/08 | (2006.01) | |
| A61K 35/74 | (2015.01) | |
| A61K 35/742 | (2015.01) | |
| A61K 35/76 | (2015.01) | |
| A61K 36/06 | (2006.01) | |
| A61K 35/00 | (2006.01) | |

(52) U.S. Cl.
CPC ............ *A61K 35/744* (2013.01); *A61K 9/006* (2013.01); *A61K 9/0034* (2013.01); *A61K 9/08* (2013.01); *A61K 35/66* (2013.01); *A61K 35/74* (2013.01); *A61K 35/742* (2013.01); *A61K 35/76* (2013.01); *A61K 36/06* (2013.01); *A61P 1/00* (2018.01); *A61P 35/00* (2018.01); *C12N 1/20* (2013.01); *A61K 2035/115* (2013.01)

(58) Field of Classification Search
CPC combination set(s) only.
See application file for complete search history.

(56) References Cited

U.S. PATENT DOCUMENTS

| 6,428,783 B1 * | 8/2002 | Khachatrian ........ A61K 35/745 |
| | | 424/93.3 |
| 8,710,184 B2 | 4/2014 | Sato et al. |
| 2013/0261071 A1 | 10/2013 | Grant et al. |

FOREIGN PATENT DOCUMENTS

| RU | 2131258 C1 | 6/1999 |
| RU | 2511044 C2 | 10/2014 |
| SU | 1743607 A1 | 6/1992 |
| WO | 2015026235 A2 | 2/2015 |

OTHER PUBLICATIONS

Smits, L. et al. Gastroenterology 2013 vol. 145, pp. 946-953.*
Communication issued by the International Searching Authority in International Patent Application No. PCT/RU2016/000845 dated Apr. 27, 2017 (International Search Report).
Communication issued by the International Searching Authority in International Patent Application No. PCT/RU2016/000845 dated Mar. 22, 2017 (Written Opinion).
Kotikovich, "Normalization of intestinal microflora helps improve brain function" Vrachu-praktiku, Sep. 4, 2013, pp. 1-3.

(Continued)

*Primary Examiner* — Heidi Reese
(74) *Attorney, Agent, or Firm* — Troutman Pepper Hamilton Sanders LLP

(57) ABSTRACT

The invention relates to microbiology and medicine and can be used to prevent and treat diseases and conditions associated with disruption of normal (autochthonous) microflora (microbiota) in humans or animals. In particular, a solution for recovery or creation of the subject's microflora comprising an active component containing microorganisms isolated from the microflora of the subject or the donor, wherein the active component can be enriched with bacteriophages of said microflora and/or additional microorganisms of the microflora cultivated on a nutrient medium, while the additional microorganisms of the microflora include microorganisms of the microflora that are yet nonculturable in the absence of the host organism, is proposed. Also provided are a pharmaceutical dosage form comprising the above solution and methods for prevention or treatment of diseases and/or conditions associated with and/or accompanied by a disorder or lack of the subject's own microflora, comprising administering the solution or pharmaceutical dosage form.

32 Claims, No Drawings
Specification includes a Sequence Listing.

(56) References Cited

OTHER PUBLICATIONS

Serova, T.V., "Bases of General Microbiology", Tutorial, Ministry of Health and Social Development of the Russian Federation, 2011, Irkutsk, IGMU.
Communication issued by the International Searching Authority in International Patent Application No. PCT/RU2016/000845 dated Jun. 5, 2018 (International Preliminary Report on Patentability), 12 pages total.
Communication issued by the European Patent Office in European Application No. 16871132.3 dated May 27, 2019, 6 pages total.
Colman, R.J. et al., "Fecal Microbiota Transplantation as Therapy for Inflammatory Bowel Disease: A Systematic Review and Meta-Analysis" Journal of Crohn's and Colitis (2014) vol. 8, pp. 1569-1581.
Smits, L.P. et al., "Therapeutic Potential of Fecal Microbiota Transplantation" Gastroenterology (2013) vol. 145, pp. 946-953.
Communication (pursuant to Article 94(3) EPC) issued by the European Patent Office in European Application No. 16871132.3 dated Nov. 24, 2020, 4 pages total.

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic Primer

<400> SEQUENCE: 1
agagtttgat ymtggctcag                   20

```
<210> SEQ ID NO 2
<211> LENGTH: 17
<212> TYPE: DNA
<213> ORGANISM: Artificial sequence
<220> FEATURE:
<223> OTHER INFORMATION: Synthetic Primer

<400> SEQUENCE: 2
attaccgcgg ctgctgg                                                    17

<210> SEQ ID NO 3
<211> LENGTH: 20
<212> TYPE: DNA
<213> ORGANISM: Artificial sequence
<220> FEATURE:
<223> OTHER INFORMATION: Synthetic Primer

<400> SEQUENCE: 3
agagtttgat ymtggctcag                                                 20

<210> SEQ ID NO 4
<211> LENGTH: 17
<212> TYPE: DNA
<213> ORGANISM: Artificial sequence
<220> FEATURE:
<223> OTHER INFORMATION: Synthetic Primer

<400> SEQUENCE: 4
attaccgcgg ctgctgg                                                    17
```

DRUGS (VARIANTS) AND METHODS FOR RESTORING MICROFLORA

CROSS-REFERENCE TO RELATED APPLICATIONS

This application is a U.S. National Phase of International Patent Application No. PCT/RU2016/000845, filed on Dec. 2, 2016, which published as WO 2017/095269 A1 on Jun. 8, 2017, and claims priority to Russian Patent Application No. 2015152096, filed on Dec. 4, 2015, all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Nov. 27, 2018, is named 244008_000078_seqlist_ST25.txt and is 1,104 bytes in size.

TECHNICAL FIELD

The invention relates to microbiology and medicine and can be used to prevent and treat diseases and conditions associated with disruption of normal (autochthonous) microflora (microbiota) in humans or animals.

BACKGROUND

A wide range of diseases that can be caused or accompanied by changes in the autochthonous microflora or microbiota (hereinafter, the term "microflora" will be used interchangeably with the term "microbiota") is known from the prior art. This is due to the important role that the microbiota plays in maintaining life and health in humans and animals. It is established that the microbiota stimulates peristalsis and renewal of intestinal cells, promotes elimination of pathogenic microorganisms, stimulates immunity, produces various molecules necessary for a macroorganism, including some vitamins, participates in digestion, inactivates biologically active components (biogenic amines), etc.

Many diseases of different localization, which are accompanied or can be caused by changes in the autochthonous microflora, are revealed. These include ulcerative colitis, irritable bowel syndrome, intestinal permeability syndrome, mucosal candidiasis, intestinal dysfunction, flatulence, vaginosis, etc. Particular danger is represented by changes in the autochthonous microflora arising on the background of hormonal disorders, prolonged antibiotic therapy, X-ray and chemotherapy, the effects of cytostatics and other drugs used in transplantology, treatment of oncology diseases, as well as a result of use of antitumor drugs. In addition, recovery of the microflora improves overall well-being and thereby improves the quality of life.

To eliminate these disorders, various methods for recovering the genuine microflora have been proposed, including by means of preparations prepared from individual bacteria of autochthonous microflora (in particular, bifido- and lactobacilli), complexes of bacteria and bacterial complexes without their reproduction, obtained from the feces of healthy people (see U.S. Pat. No. 6,572,854, "Use of bacteria endowed with arginine deiminase to induce apoptosis and/or reduce an inflammatory reaction and pharmaceutical preparations containing such bacteria"; U.S. RE39,892, "Pharmaceuticals containing lactobacilli for the treatment of vaginal infections and related method") or from various bacteria found in faeces (see e.g., U.S. Pat. No. 6,428,783 "Bank of autochthonous strains of microorganisms and methods of its use for recovery of intestinal microbiocenosis of the men").

The disadvantages of the known technical solutions is the lack of a systematic approach, the low effectiveness of treatment of dysbacteriosis caused by the use of either the whole intestinal microflora as a whole or some of the traditionally used strains, mainly strains of bifido- and lactobacilli, and the lack of scientific research on the role of various microorganisms and their different effectiveness to restore the genuine microflora, which in general did not allow to create a solution providing a high efficiency treatment of dysbiosis and rapid recovery of the body's own microflora, up to now.

Based on sources of scientific, technical and patent information, the possibility of creating such a bank of autochthonous strains of microorganisms is unknown, which, on the one hand, would be uniform regardless of the source of its production, and on the other hand, would allow obtaining reproducible and predictable results in restoring human intestinal microbiocenosis.

It is the object of the present invention to provide a method for the preparation of a medicament which, on the one hand, would be individualized and contain autochthonous microorganisms inherent to the particular individual, highly effective for restoring his/her intestinal microflora, and on the other hand would have a constant composition and provide well reproducible and predictable results.

The present invention is based on the results of scientific research obtained by the authors in the course of studying the composition of autochthonous microflora of various localizations. In particular, during these studies, it was unexpectedly found that the microflora of the gastrointestinal tract, in particular the intestinal mucosa, oral cavity and skin, has a very similar or identical qualitative composition of certain microorganisms, which are conditionally called the "microflora core". As a result of the research, it was unexpectedly found that the examined samples of saliva, skin, and feces contain representatives of the same taxa of microorganisms: in particular, Actinomycetales, Bacteroidales, Flavobacteriales, Bacillales, Lactobacillales, Clostridiales, Erysipelotrichales, Selenomonadales, Fusobacteriales, Neisseriales, Campylobacterales, Pasteurellales. While the qualitative composition is similar, the differences concern only the quantitative representation of certain microbes depending on their localization in the human body. Perhaps, different conditions are preferable for certain microbes, while others are present in a small amount, but do not disappear completely.

Further, studies conducted during the development of the present invention have shown that the autochthonous microflora is maternally inherited, as is the case of human inheritance of mitochondria. Thus, at least mitochondria and the nucleus of the microflora of children, regardless of their sex, are received from their mother.

An additional study was dedicated to studying the role of bacteriophages in the occurrence of changes in microflora, which are called "microflora diseases". It is known that a normal microflora contains 10 times more bacteriophages than bacteria. Bacteriophages play an important role in maintaining the homeostasis of normal microflora. At the same time, people constantly receive a large number of additional bacteriophages from the environment with food, beverages and in contact with other objects and subjects; these additional bacteriophages are capable of causing undesirable changes in the microflora that can lead to a pathological state of the macroorganism. In experiments conducted by the authors of the invention, the introduction of certain phages into food for animals resulted in appearance of a pathological syndrome, which manifests itself in the form of various lesions of the heart, kidneys, pancreas, and oncological diseases.

Based on these new data, the authors developed a solution and a method for prevention and treatment of diseases associated with impaired functions and/or composition of the normal microflora.

SUMMARY OF INVENTION

The object of the invention is to develop a new solution and method for recovery or creation of a normal autochthonous microflora.

This object is achieved by preparation of a medicament for recovery or creation of the microflora of the subject consisting of a composition obtained from microorganisms isolated from the normal genuine microflora of healthy humans, with microorganisms isolated from the microflora of the oral cavity (saliva, mucous membranes), other sections of the gastrointestinal tract (intestines, stomach, etc.), skin, feces. Additionally, along with microflora bacteria, bacteriophages of microflora can be collected, stored and used. Before use, the solution can be enriched with the genuine bacteria grown on a rich nutrient medium under aerobic and anaerobic conditions, after seeding the stored microbiota samples.

The carrier individual (genuine microflora), mother, sisters and brothers of the whole blood, as well as relatives on the maternal side (mother's sisters and their children, all descendants in the first generation, children of daughters in the second generation, etc.) can all act as donors of microflora, as well as other donors in the absence of the listed. The genuine microflora can be sampled from the subject in childhood and adolescence.

The solution can be prepared directly when it is necessary, and can be prepared in advance and stored in a microflora bank.

According to one of the aspects of the invention, a solution for recovery or creation of the subject's microflora is provided comprising an active component comprising microorganisms isolated from the subject's own microflora or a microflora of a donor selected from the group comprising his/her mother and/or other relatives on the maternal side.

According to one of the embodiments, microorganisms are bacteria isolated from the subject's own microflora or a microflora of a donor selected from the group comprising his/her mother and/or other relatives on the maternal side.

According to one of the embodiments, the solution may comprise at least one microorganism selected from microorganisms belonging to: Actinomycetales, Bacteroidales, Flavobacteriales, Bacillales, Lactobacillales, Clostridiales, Erysipelotrichales, Selenomonadales, Fusobacteriales, Neisseriales, Campylobacterales, Pasteurellales.

According to one of the embodiments, the solution may further comprise at least one microorganism selected from the following group: Aerococcaceae, Burkholderiaceae, Carnobacteriaceae, Coriobacteriaceae, Erysipelotrichaceae, Eubacteriaceae, Lachnospiraceae, Leptotrichiaceae, Micrococcaceae, Peptostreptococcaceae, Porphyromonadaceae, Prevotellaceae, Pseudomonadaceae, Ruminococcaceae, Streptococcaceae, Veillonellaceae.

According to one of the embodiments, the solution may further comprise archaea and fungi isolated from the subject's own microflora or a microflora of a donor selected from the group comprising his/her mother and/or other relatives on the maternal side.

According to one of the embodiments, microorganisms are bacteriophages isolated from the subject's own microflora or a microflora of a donor selected from the group comprising his/her mother and/or other relatives on the maternal side.

According to one of the embodiments, microorganisms are bacteria and bacteriophages isolated from the subject's own microflora or a microflora of a donor selected from the group comprising his/her mother and/or other relatives on the maternal side.

According to one of the embodiments, the ratio of bacteria to bacteriophages is selected from the following list: 1000:1 to 100:1, 100:1 to 10:1, 10:1 to 1:10; 1:10 to 1:100; 1:100 to 1:1000.

According to one of the embodiments, the active component in the solution referred to above is enriched with additional microorganisms of the microflora grown on a nutrient medium, the additional microorganisms of the microflora including microflora microorganisms not yet cultivated in absence of the host organism.

According to one of the embodiments, the solution in compliance with any of the above-described aspects further comprises at least one pharmaceutically acceptable excipient.

According to one of the embodiments, a pharmaceutically acceptable excipient is selected from the group consisting of the following: isotonic sodium chloride, activated carbon, silica, chalk, sugar, lactose, gelatin, starch, polyvinyl alcohol (PVA), polyvinylpyrrolidone (PVP), cellulose, methyl cellulose (MC), hydroxypropylmethyl cellulose (CMO), carboxymethyl cellulose (CMC), sodium carboxymethylcellulose (Na—CMC) and other substances conventionally used as pharmaceutically acceptable excipients.

According to one of the embodiments, the active component is obtained by cultivation of at least a portion of the microorganisms isolated from the microflora of the subject or the microflora of the donor under aerobic and/or anaerobic conditions.

According to one of the embodiments, the active component is obtained by cultivation of at least 100 to 1000 bacteria per ml, 1000 to 10,000 bacteria per ml, $10^3$ to $10^5$ bacteria per ml, $10^5$ to $10^7$ bacteria per ml, $10^7$ to $10^9$ bacteria per ml, $10^9$ to $10^{12}$ bacteria per ml or more bacteria per ml.

According to one embodiment, the active component contains microorganisms isolated from a microflora derived from saliva, mucous membranes, skin, gastrointestinal tract, and/or feces, with the addition of microorganisms from this microflora cultivated on a nutrient medium and added immediately before administration of the solution.

According to one of the embodiments, the active component contains microorganisms isolated from the microflora of saliva, mucous membranes, skin, gastrointestinal tract, and/or feces collected at the time preceding the moment of the impact on the body of the subject that may affect the composition of normal microflora.

According to one embodiment, the active component contains microorganisms isolated from a microflora derived from the genuine microflora of the subject or from the microflora of the donor, with the addition of microorganisms from this microflora cultivated on a nutrient medium and added prior to administration of the solution. In particular, microorganisms intended to be added to the active component for its enrichment can be cultivated on a nutrient medium and added in a period of 1 hour to 80 years, approximately one hour, in a period of 1 hour to 1 day, approximately 1 day, in a period of 1 day to 1 month, approximately 1 month, in a period of one month to one year, approximately 1 year, or in a period of 1 to 80 years prior to the beginning of administration of the solution.

According to one of the embodiments, the time point preceding the moment of the beginning of the effect on the subject's body is a point of time in the childhood/juvenile age of the subject.

According to one of the embodiments, the active component is formulated in a form suitable for freezing and long-term storage.

According to one of the embodiments, the solution further comprises auxiliary substances that reduce fluidity.

According to one of the embodiments, the fluidity reducing auxiliary substances are selected from the group consisting of latex, sorbent, polyethylene glycol, agar-agar, gelatin, microbial nutrient media and other substances capable of reducing fluidity.

According to one of the embodiments, the solution further comprises microflora bacteria that enhance the ability of microorganisms to colonize certain areas of the skin or mucosa.

According to another embodiment, the solution contains bacteria that ensure colonization resistance, in particular, produce substances that inhibit the development of foreign microbes, and do not influence or contribute to the development of their own strains and species, thereby creating associations of microorganisms that have beneficial effects on the vital activity of the organism in general.

In yet another aspect, a pharmaceutical dosage form for the prevention and/or treatment of diseases and/or conditions associated with and/or accompanied by a disorder or lack of the subject's own microflora is provided, comprising a solution according to the described aspect and embodiments, and a pharmaceutically acceptable excipient.

According to one of the embodiments, the solution or the pharmaceutical dosage form can be prepared in the form of capsules, tablets, pellets, caplets, powder, aerosol, lyophilizate, gel, suspension cream, emulsion, suspension in a nutrient medium or other suitable liquid, for example, in water.

According to one of the embodiments, the solution or pharmaceutical dosage form can be prepared in a form selected from those suitable for dissolution in the oral cavity, small intestine, stomach, colon, buccal or sublingual administration forms, forms for transmucosal administration, for example, using an endoscope or in forms for intravaginal administration.

In yet another aspect, a complex for the prevention and/or treatment of diseases and/or conditions associated with and/or accompanied by a disorder or lack of the subject's own microflora is provided, comprising the solution or at least one pharmaceutical dosage form according to any of the described aspects, and instructions for administering to the subject.

In yet another aspect, a method for the prevention and/or treatment of diseases and/or conditions associated with and/or accompanied by a disorder or lack of the subject's own microflora is provided, comprising administering the solution or a pharmaceutical dosage form according to any of the described aspects to the subject requiring that.

According to the exemplary embodiments, the proposed method is designed to rapidly create a normal microbiota in babies delivered by Caesarean section, while the active component contains microorganisms isolated from the mother's microflora or the microflora of another relative on the maternal side.

According to the exemplary embodiments, the proposed method is designed to rapidly create a normal microbiota in babies delivered naturally by a surrogate mother, while the active component contains microorganisms isolated from the genetic mother's microflora or the microflora of her relative.

According to the exemplary embodiments, the method of the present invention is intended for prevention and/or treatment of increased intestinal permeability and/or correction of the leaky gut syndrome, while the active component comprises microorganisms isolated from the subject's own microflora prior to the induction of the intestine permeability enhancement and/or microflora of his/her relatives on the maternal side at a young age, and the microorganisms include bacteria isolated from said microflora, bacteria combined with bacteriophages isolated from said microflora, as well as isolated bacteriophages isolated from said microflora.

According to the exemplary embodiments, the method of the invention is intended to restore the composition of the subject's microflora with an increase in the life span of the subject, while the active component comprises microorganisms isolated from the subject's own microflora earlier or microflora of his/her relatives on the maternal side at a young age, and the microorganisms include bacteria isolated from said microflora, bacteria combined with bacteriophages isolated from said microflora, as well as isolated bacteriophages only isolated from said microflora.

According to the exemplary embodiments, the method of the invention is intended for prevention and/or treatment of tumor diseases in the subject, while the active component comprises microorganisms comprising bacteria and/or bacteriophages obtained from the microflora of said subject earlier or microflora of his/her relatives on the maternal side at a young age.

According to exemplary embodiments of any of the described aspects, diseases and/or conditions associated with and/or accompanied by a disorder or lack of microflora in the subject are selected from the group consisting of ulcerative colitis, irritable bowel syndrome, intestinal permeability syndrome, mucosal candidiasis, bowel dysfunction, flatulence, vaginosis, tumor diseases; diseases and/or conditions that occur against the background of hormonal disorders, long-term antibiotic therapy, X-ray and chemotherapy, the effects of cytostatics and drugs used in transplantology, as a result of use of antitumor drugs; diseases and/or conditions associated with delivery by Caesarean section and the birth from a surrogate mother in the natural manner.

Furthermore, a method for stimulating the immune system of an organism weakened by diseases and/or conditions associated with and/or accompanied by a disorder or lack of the subject's own microflora is provided, comprising administering the solution or a pharmaceutical dosage form according to any of the described aspects.

According to an aspect of the invention, use of the solution according to the described aspects is proposed for the restoration and/or creation of the subject's microflora.

According to another aspect of the invention, use of the solution according to the described aspects is proposed for prevention and/or treatment of diseases and/or conditions associated with and/or accompanied by a disorder or lack of the subject's own microflora.

According to another aspect of the invention, use of the solution comprising microorganisms isolated from the subject's organism, including bacteria and/or bacteriophages obtained from the microflora of the same subject, or obtained from the microflora of his/her relatives on the maternal side at a young age, is proposed to restore the microflora of the subject and increase the life span.

According to another aspect of the invention, use of the solution comprising microorganisms isolated from the subject's organism, including bacteria and/or bacteriophages obtained from the microflora of the same subject, or obtained from the microflora of his/her relatives on the maternal side at a young age, is proposed to prevent and/or treat increased intestinal permeability and to eliminate symptoms of increased intestinal permeability.

DETAILED DESCRIPTION OF THE INVENTION

In the present description, the terms "microflora", "microbiota", "microbiocenosis" are interchangeable and refer to the totality of various types of microorganisms inhabiting any habitat.

In the present description, the terms "microbe" and "microorganism" are interchangeable and refer to a group of living organisms whose dimensions are, in particular, less than 1 mm. They include, in particular, protozoa, bacteria, viruses, fungi, yeast.

Viruses, in turn, include bacteriophages, which are viruses of bacteria.

Nonculturable or yet nonculturable forms of microorganisms are those forms of microorganisms that, in the absence of the host organism or in response to the influence of unfavorable factors, stop growth on nutrient media, but remain viable, and with improved cultivation conditions, resume their proliferation. In other words, in this case, the microorganisms pass into a nonculturable state, in which they can be for a long time. The term "yet nonculturable" or "previously nonculturable", referring to microorganisms, means that at the time of preparation of this application the possibility to ensure growth of such microorganisms on a nautrient media in the absence of the host organism is not known (see, for example, Colwell, R., Grimes J. "Nonculturable Microorganisms in the Environment", ASM Press, 2000. pp. 2-3).

According to one of the aspects of the invention, a solution for recovery or creation of the subject's microflora is provided comprising an active component comprising microorganisms isolated from the subject's own microflora or a microflora of a donor selected from the group comprising his/her mother and/or other relatives on the maternal side and, in addition, a component that enhances the effect of the solution.

According to one of the embodiments, microorganisms are bacteria isolated from material obtained from the subject or a donor, as well as archaea and/or fungi isolated from the subject's own microflora or microflora of a donor selected from the group comprising his/her mother and/or relatives on the maternal side, and additionally, a component that enhances the effect of the solution.

According to one of the embodiments, as an additional component enhancing the effect of the solution, the solution further comprises bacteriophages isolated from material obtained from the subject or a donor.

According to one of the embodiments, the material obtained from the subject or donor can be a material derived from the oral cavity (saliva, scrapings, mucus washings, sputum), other parts of the gastrointestinal tract (GT) (esophagus, stomach, intestines), feces, skin, respiratory tract, genital organs, urethra, conjunctiva, external auditory canal.

According to one of the embodiments, the ratio of bacteria isolated from the genuine microflora to bacteriophages isolated from the genuine microflora in the solution is 1000:1 to 1:1000.

According to one of the embodiments, the ratio of bacteria to bacteriophages in the solution is selected from the following list: 1000:1 to 100:1, 100:1 to 10:1, 10:1 to 1:10; 1:10 to 1:100; 1:100 to 1:1000. According to one of the embodiments, as an additional component enhancing the effect of the solution, the solution further comprises microflora bacteria cultivated on a nutrient medium comprising yet nonculturable forms of microorganisms of the microflora.

According to one of the embodiments, the solution further comprises both bacteriophages isolated from the material obtained from the subject or a donor, and additional microorganisms of microflora cultivated on a nutrient medium, comprising yet nonculturable forms of microorganisms of the microflora.

The additional microorganisms referred to may be cultivated on a nutrient medium in advance and stored prior to addition to the active component under suitable conditions, wherein addition of said additional microorganisms can be performed immediately prior to administration, in particular about 1 hour, about 1 day before administration of the solution.

According to one of the embodiments, the microflora can be a normal microflora of healthy people, including but not limited to, the microflora of the oral cavity (saliva, scrapings, mucus washings, sputum), other parts of the gastrointestinal tract (GT) (esophagus, stomach, intestines), feces, skin, respiratory tract, genital organs, urethra, conjunctiva, external auditory canal. The carrier individual (genuine microflora), sisters and brothers of the whole blood, mother, as well as relatives on the maternal side (mother's sisters and their children, all descendants in the first generation, children of daughters in the second generation, etc.) can all act as donors of microflora, as well as other donors in the absence of the listed (donor microflora). In one of the embodiments, the microflora is sampled from the subject or donor in childhood and adolescence.

In one of the embodiments, the subject is an animal, in particular a mammal, in particular a human of any age, including a child.

The sampling of biological material from the subject or a donor is carried out by standard methods. According to one of the embodiments, the biological material selected from the subject or a donor, for example feces, is mixed in a sterile isotonic sodium chloride solution or other suitable buffer and filtered to remove undigested food particles, after which the microorganisms are precipitated by centrifugation.

According to one of the embodiments, washings from the skin or scrapings from the mucosa are obtained by standard methods, after which a sterile isotonic sodium chloride solution or other suitable buffer is added to the biological material.

According to one of the embodiments, fresh saliva is used, for example, in a volume of 5-10 ml, into which flushing from a cotton swab that is used to collect microbes from the buccal mucosa is added. The washings from swabs are carried out with a sufficient volume of a sterile isotonic sodium chloride solution, for example 1.0 ml. As a result, it is possible to obtain the maximum variety of oral bacteria, which includes cultured and yet nonculturable microbes. Further, the procedure is similar to that used to collect microbes from another material. In particular, the obtained material can be placed in conical tubes, after which rapid precipitation by centrifugation is carried out. To the resulting precipitate, an isotonic sodium chloride solution can be added and individual doses comprising 0.001 to 10.0 ml of the original microbial mixture.

According to one of the embodiments, bacteriophage from the subject or a donor material, after removing bacteria from the material, it is filtered through a filter with a pore size of 0.17-0.25 µm, after which the phages are washed off the filter with a minimum amount of the buffer used or an isotonic sodium chloride solution.

The volume of biological material taken from the subject or a donor is determined depending on the age of the subject or the donor and the location of the material sampling. A person skilled in the art will determine the required volume of material based on the type of biological material, the preparation method of the drug, the pharmaceutical form and the type of administration, as well as other factors.

In this description, the terms "previously sampled", "previously obtained", and "previously isolated", relating to the microflora and/or microorganisms of the present invention, mean in particular that the material, microflora or microorganisms are selected, obtained or isolated from the subject or a donor before the beginning of restoration or creation of microflora in the subject, prevention or treatment of diseases and conditions associated with and/or accompanied by a disorder or lack of the subject's own microflora, before exposure of the subject's organism that can lead to the disorder, damage or destruction of the microflora of the subject, and also before the onset of the development of the disease or condition associated with and/or accompanied by a disorder or lack of the subject's own microflora.

The microflora obtained from the subject or a donor can be used immediately or stored, in particular in a microflora bank.

The microflora or the solution can be stored under a variety of conditions, including, but not limited to, the following: at a temperature of about −70° C. to −80° C., the liquid nitrogen temperature or in the form of a lyophilized dried preparation. According to the embodiments, samples of microflora or the solution can be stored frozen in separate vials for later use.

For storage of samples of the selected microflora, stabilizers can be added to ensure their long-term preservation, which can be controlled (for example, for maximum of once a year) during the storage period by the ability to grow on a nutrient medium specially developed by the authors. According to one of the embodiments, the stabilizers are selected from the group comprising glycerin and other potential (commercial) stabilizers.

According to one of the embodiments, the solution is obtained by sampling biological material (including saliva, sputum, faeces) from healthy subjects and/or donors (e.g., relatives on the maternal side), removing non-bacterial impurities from it, storing the resulting material as separate samples during the life of the subject or a donor. The number of bacteria in the samples can be from $10^1$-$10^{10}$, for example, $10^1$ to $10^3$, $10^1$ to $10^5$, $10^3$ to $10^5$, $10^5$ to $10^7$, $10^6$ to $10^8$, $10^7$ to $10^{10}$, $10^3$ to $10^7$, and the amount of bacteriophages in the samples can be from $10^1$-$10^{12}$ in 1 ml/sample, for example, $10^1$ to $10^3$, $10^1$ to $10^5$, $10^3$ to $10^5$, $10^5$ to $10^7$, $10^6$ to $10^8$, $10^7$ to $10^{10}$, $10^3$ to $10^{12}$ in 1 ml/sample.

According to one of the embodiments, the solution can be used for oral, enteral, local, buccal, sublingual, duodenal, transmucosal, intravaginal, and rectal administration, in particular in the form of enemas.

According to one of the embodiments, the solution according to the described aspects, containing strains of autochthonous microflora of healthy people, allows to restore the damaged bacteriobiocenosis in the case of disorders of its own microflora associated with a disease, administration of antibiotic, age, etc.

Administration to a subject of the solution containing microorganisms isolated from the autochthonous microflora of the subject or the microflora of a donor enriched with bacteriophages isolated from the biological material collected from the subject and/or the donor and/or additional microorganisms of the microflora cultivated on a nutrient medium containing microflora of yet nonculturable microorganisms, allows you to quickly and efficiently restore the microflora of the subject's body by means of microorganisms and bacteriophages inherent in this particular subject.

Enrichment of the solution with additional microorganisms of the microflora cultivated on a nutrient medium, including yet nonculturable microorganisms of the microflora, allows to reach the concentrations of microorganisms in the medium that are as close as possible to the concentrations of microorganisms in the organism of the subject in the healthy state.

According to one of the embodiments, the active component can be obtained by cultivation of at least some part of the microflora, for example, at least 100 bacteria per ml, or a larger amount of up to $10^{12}$ bacteria per ml under aerobic or anaerobic conditions.

According to the exemplary embodiments, the active component can be obtained by cultivation of at least 100 to 1000 bacteria per ml, 1000 to 10,000 bacteria per ml, $10^3$ to $10^5$ bacteria per ml, $10^5$ to $10^7$ bacteria per ml, $10^3$ to $10^9$ bacteria per ml, $10^9$ to $10^{12}$ bacteria per ml or more bacteria per ml under aerobic or anaerobic conditions.

According to the exemplary embodiments, the active component may be present in the composition of the solution in any amount that is capable of providing the desired effect according to the described aspects and embodiments, for example in an effective amount. A medical specialist will be able to easily choose an appropriate amount of the active component for the solution according to the present invention, which is necessary to achieve the desired effect.

With age, the number of microorganisms and bacteriophages of microflora may decrease. Accordingly, in one of the embodiments, the microflora of the subject or a donor is sampled from the subject or the donor in childhood or adolescence. Administration of the microflora sampled in childhood and adolescence to the subject can contribute to a more rapid and more effective recovery of the microbiocenosis of the subject's body.

In some cases, it is sufficient to introduce only bacteriophages that are inherent in the subject's body. Bacteriophages are viruses of bacteria, they contribute to their variability and adaptation, and also can cause their death. Possessing high sensitivity, they selectively affect certain types of bacteria, without harming the normal intestinal microflora. Accordingly, bacteriophages can be used to treat and prevent diseases and conditions associated with a disorder of the normal biocenosis of the body.

It is known to use bacteriophages to enhance the therapeutic effect and restore the normal microflora. In the absence of bacteria sensitive to bacteriophage, the duration of their stay in the human body is no longer than 1-3 days. They give few adverse reactions and complications, increase the effectiveness of treatment with various antibacterial drugs, increase immunity. It is known that bacteriophages can be used to treat dysbacteriosis in newborns and children in the first year of life.

However, known drugs for the treatment of microflora disorders using bacteriophages have a number of disadvantages. As far as is known to the authors of the present invention, the available preparations based on bacteriophages are narrowly specific due to the use of specific phages that destroy certain types of bacteria. In addition, the body quickly develops phage-resistant strains, so in this case treatment cannot be prolonged. Also, bacteriophages can cause allergic reactions.

In contrast to the known preparations using bacteriophages, the present invention employs bacteriophages isolated from a material obtained from the subject or a donor on the maternal side. This allows to increase the efficiency of microflora recovery, eliminate allergic reactions and also, in special cases of implementation, provide a complex effect on the organism in which the active components of the composition according to the invention enhance each other's action, in particular, the presence of bacteriophages along with the bacteria of the genuine microflora can help suppress the development of foreign microorganisms and promote restoration of the normal microflora of the subject.

According to the exemplary embodiments, the solution may be a single-component or multi-component, for example, may be presented in the form of a composition or a formulation, including a pharmaceutical composition or a formulation, and a drug, optionally containing at least one pharmaceutically acceptable vehicle and/or excipient.

According to one of the embodiments, a pharmaceutically acceptable vehicle and/or excipient is selected from the group consisting of the following: sodium chloride (for example, as an isotonic solution), activated carbon (e.g., activated carbon powder), silica, chalk (e.g., suspension of chalk particles), sugar, lactose, gelatin, starch, polyvinyl alcohol (PVA), polyvinylpyrrolidone (PVP), cellulose, methyl cellulose (MC), hydroxypropylmethyl cellulose (CMO), carboxymethyl cellulose (CMC), sodium carboxymethylcellulose (Na—CMC) and other substances conventionally used as pharmaceutically acceptable vehicles and/or excipients.

Pharmaceutical Dosage Forms

According to one of the embodiments, a pharmaceutical dosage form for recovery and/or creation of a microflora of a subject, as well as for the prevention and/or treatment of diseases and/or conditions associated with and/or accompanied by a disorder or lack of the subject's own microflora is provided, comprising a solution according to the described aspect and embodiments, and a pharmaceutically acceptable excipient.

Pharmaceutical dosage forms can be prepared in the form of capsules, tablets, pellets, caplets, powder, water suspension, suspension in a nutrient medium or other suitable liquid, suspensions, emulsions, aerosols, gel, lyophilisate, cream.

Pharmaceutical dosage forms can be prepared in a form intended for oral, enteral, local, buccal, sublingual, duodenal, transmucosal, intravaginal, rectal administration. According to exemplary embodiments of the invention, pharmaceutical dosage forms are proposed prepared in a form suitable for dissolution in the oral cavity, small intestine, stomach, large intestine.

According to embodiments of the invention, dosage forms suitable for buccal or sublingual administration, for transmucosal administration, for example, by means of an endoscope, for intravaginal administration, are proposed.

According to exemplary embodiments, the proposed solution and/or pharmaceutical forms can be used to treat diseases and/or conditions associated with and/or accompanied by a disorder or lack of microflora in the subject selected from the group consisting of ulcerative colitis, irritable bowel syndrome, intestinal permeability syndrome, mucosal candidiasis, bowel dysfunction, flatulence, vaginosis, tumor diseases; diseases and/or conditions that occur against the background of hormonal disorders, long-term antibiotic therapy, X-ray and chemotherapy, the effects of cytostatics and drugs used in transplantology, as a result of use of antitumor drugs; diseases and/or conditions associated with delivery by Caesarean section and the birth from a surrogate mother in the natural manner.

In yet another aspect, a complex for the prevention and/or treatment of diseases and/or conditions associated with and/or accompanied by a disorder or lack of the subject's own microflora is provided, comprising the solution or at least one pharmaceutical dosage form according to the described aspects and exemplary embodiments, and instructions for administering to the subject.

Pharmaceutical dosage forms (a drug, a preparation) for administration to the subject can be prepared by standard methods.

According to one of the embodiments, for the preparation of an enteric dosage form in the form of enteric-soluble capsules, powder of activated carbon or silica, or a suspension of chalk particles or cellulose particles, or other filler may be added to create a consistent mixture suitable for filling the capsules. According to one of the embodiments, the solution is administered orally with a duration determined by the subject's condition and the type of pathology.

For enteral administration, liquid dosage forms can also be used. Such forms can be prepared by diluting microflora samples with water or another liquid suitable for drinking. The subject receives the drug in the form of drops or a liquid for drinking. The preparation can be enriched with various consistent food additives to give it a gel-like form and/or with flavoring nutritional supplements.

The preparation can also be administered to the intestine rectally, for example, by enemas, or orally, for which the samples are diluted with water or another liquid suitable for such an administration route, and the subject receives the drug in the form of drops or a liquid for drinking.

For the local application of the medicament, for example for application to the skin or mucous membranes, permitted (for example, pharmaceutically acceptable) substances may be added to the microbial material to impart the desired consistency and/or adhesive properties and/or taste and/or color, and/or other cosmetically important and customer-related properties.

Methods for Restoring the Composition of Microflora

According to the invention, methods for recovering the composition of or creating an organism microflora that has been impaired or weakened by diseases and/or conditions associated with and/or accompanied by a disorder or lack of the subject's own microflora is provided, comprising administering the solution or a pharmaceutical dosage form according to any of the described aspects.

According to the exemplary embodiments, diseases and/or conditions associated with and/or accompanied by a disorder or lack of genuine microflora in the subject are selected from the group consisting of ulcerative colitis, irritable bowel syndrome, intestinal permeability syndrome, mucosal candidiasis, bowel dysfunction, flatulence, vaginosis, tumor diseases; diseases and/or conditions that occur against the background of hormonal disorders, long-term antibiotic therapy, X-ray and chemotherapy, the effects of cytostatics and drugs used in transplantology, as a result of use of antitumor drugs; diseases and/or conditions associated with delivery by Caesarean section and the birth from a surrogate mother in the natural manner.

According to the exemplary embodiments, tumor diseases are diseases caused by the transformation of normal cells of organs and tissues into tumor cells prone to uncontrolled proliferation. Such diseases include benign and malignant neoplasms and can be manifested in the form of (including but not limited to) a fibroma, myoma, osteoma, lipoma, cancer, carcinoma, sarcoma, blastoma, lymphoma, leukemia, melanoma, teratoma or glioma of any organ, for example, the organ of the gastrointestinal tract, the urinary system, respiratory system, nervous system, integumentary system, musculoskeletal system, cardiovascular system, hematopoiesis system, and in particular, intestinal tumors, including small intestine, large intestine, straight intestine, dodecadactylon; ventricle, esophagus, liver, pancreas, oral cavity and pharynx, gallbladder, heart, larynx, lung, breast, skin, ovary, prostate, uterus, thyroid, brain and spinal cord.

According to the invention, the proposed method comprises administration of the microorganisms comprising bacteria isolated from a normal genuine microflora of a healthy subject or microflora of a donor from the maternal side. Additionally, bacteriophages of microflora can be used for treatment together with microflora bacteria, and also, before starting the treatment, the preparation can be enriched with genuine bacteria cultivated on a rich nutrient medium under aerobic or anaerobic conditions, after seeding stored samples of the treated subject's microflora or microflora of his/her relatives on maternal side.

According to one of the embodiments, the method for recovering the composition of or creating an organism microflora that has been impaired or weakened by diseases and/or conditions associated with and/or accompanied by a disorder or lack of the subject's own microflora, comprises the following:
- collection of a sample of the normal microflora of the subject, and/or microflora of the donor selected from the relatives of the subject, for example, relatives on the maternal side;
- preparation of a solution containing microorganisms isolated from the subject's own microflora and/or that of his/her relatives, for example, relatives on the maternal side, including bacteria isolated from microflora, and/or bacteria together with bacteriophages isolated from microflora and/or only isolated bacteriophages isolated from microflora;
- affecting the subject, where undesirable disturbance of his/her microflora occurs;
- administration of an effective amount of the solution prepared over a period of time sufficient to restore normal microflora to the subject.

The regimen of administration of microflora can span from one day to one year, possibly from 1 day to 10 days, from 10 days to 20 days, from 10 days to 30 days, and more.

According to one of the embodiments, a method of prevention and treatment is provided comprising administering the solution or a pharmaceutical form as described above for a period of 1-5 days, with a break for 1-20 days, then a repeated administration for 1-5 days.

In one of the embodiments, a method of prevention and treatment is provided comprising administering the solution or a pharmaceutical form as described above for a period of 5-10 days, with a break for 1-20 days, then a repeated administration for 5-10 days, and then, if necessary, the above cycle is repeated once more.

According to one of the embodiments, the subject's normal microflora is sampled prior to initiating exposure of the subject that may cause a disruption in the composition of the microflora, for example, prior to initiation of antibiotic treatment, or prior to initiation of treatment with other drugs that may cause microflora damage or exposure to radiation; in such cases, as for example, the effect on benign or malignant tumors, samples of microflora are obtained from the subject to whom such treatment is prescribed, which are stored in the corresponding conditions before the end of the damaging effects. Upon termination of the damaging exposure, a preparation containing bacteria isolated from the healthy microflora of the subject is prepared, as described above, to restore the normal microflora of the subject.

Alternatively, it is possible that at the time of the encounter with the specialist, the subject has already been treated with drugs that result in a microflora disorder, or the subject has been exposed to radiation resulting in a disturbance of the normal microflora, for example in the event of an accident at a nuclear power plant, accident elimination operations, accidental exposure to a damaging radiation, or treatment, such as proton, photon therapy, or exposure to other type of radiation. In this case, if there is no possibility to collect samples of the normal microflora of the subject, a method of treatment using the microflora of a donor selected from the relatives of the subject, for example, relatives on the maternal side, including mother, the mother's sisters and other relatives on the maternal side, may be chosen.

According to one of the embodiments, the method for recovering the composition of the body microflora that has been impaired or weakened by diseases and/or conditions associated with and/or accompanied by a disorder or lack of the subject's own microflora, comprises the following:
- collection of the microflora of the donor selected from the relatives on the maternal side of the subject;
- preparation of a solution containing microorganisms isolated from the microflora of a relative of the subject on the maternal side, including bacteria isolated from microflora, and/or bacteria together with bacteriophages isolated from microflora and/or only isolated bacteriophages isolated from microflora;
- administration of an effective amount of the solution prepared over a period of time sufficient to restore normal microflora to the subject, as described above.

In one of the embodiments, a method for recovery of the subject's microflora is proposed which includes a planned exposure of the subject's microflora to reduce or destroy a pathogenic microflora, followed by recovery of the microflora using a microflora obtained from a healthy donor on the maternal side.

According to one of the embodiments, the method for recovering the composition of the body microflora that has been impaired or weakened by diseases and/or conditions associated with and/or accompanied by a disorder or lack of the subject's own microflora, comprises the following:
- implementation of an impact on the subject causing the disorder, weakening or destruction of hi s/her microflora;
- collection of the microflora of the donor selected from the relatives on the maternal side of the subject;
- preparation of a solution containing microorganisms isolated from the microflora of a relative of the subject on the maternal side, including bacteria isolated from microflora, and/or bacteria together with bacteriophages isolated from microflora and/or only isolated bacteriophages isolated from microflora;

administration of an effective amount of the solution prepared over a period of time sufficient to restore normal microflora to the subject, as described above.

According to one of the embodiments, a method for stimulating the immune system of an organism that has been impaired or weakened by diseases and/or conditions associated with and/or accompanied by a disorder or lack of the subject's own microflora is provided, comprising administering the solution or a pharmaceutical dosage form according to any of the described aspects.

According to another aspect of the invention, a method is provided intended for recovery of the microflora composition and increasing the life span of the subject by administering microorganisms obtained from the genuine microflora of the subject or that of his/her relatives on the maternal side at a young age, including bacteria obtained from the microflora and/or bacteria together with bacteriophages, obtained from the microflora, and/or only isolated bacteriophages obtained from the microflora.

According to another aspect of the invention, a method is provided intended for reducing increased intestinal permeability and/or correcting the syndrome of increased intestinal permeability by administering microorganisms obtained prior to induction of increased intestinal permeability from the genuine microflora of the subject or that of his/her relatives on the maternal side, including bacteria obtained from the microflora and/or bacteria together with bacteriophages, obtained from the microflora, and/or only isolated bacteriophages obtained from the microflora.

The invention is illustrated by the following examples, which do not limit the scope of the present invention, but are intended merely to explain possible ways of implementing the invention, which will be apparent to those skilled in the art upon reading this description.

EXAMPLES

Example 1

Inheritance of the Microbiota Nucleus on the Maternal Side

To determine the transfer of the microbiota nucleus on the maternal side, the authors conducted a comparative study of the composition of the microflora of the members of the family chosen for the study and determined the degree of its similarity. Family structure:

Mother, 29
Father, 31
Son, 3
Daughter, 2

The DNA was isolated from the samples using DNASorb B kit (InterLabService, Russia). Amplification was carried out using universal bacterial primers flanking the V1-V3 region of the 16S rRNA gene—9F and 541R. Metagenomic sequencing of the fragment of the 16S rRNA gene was carried out on a Roche-454 Genome Sequencer FLX Ti pyrosequencer.

As a result of the study, 53492 readings were obtained, which means that the average coverage was 53492/4 samples=13373 readings.

To assess the similarity of the microbiotic profile (Table 1), UniFrac analysis was used. At that, only the types of microorganisms represented in all members of the family were taken into account to evaluate the results of the study, that is, those microorganisms that form the core of the microflora.

TABLE 1

Similarity of microflora composition between family members, based on UniFrac analysis

| Pair for comparison | Similarity indicators |
|---|---|
| Mother/son | 0.376499 |
| Mother/daughter | 0.452154 |
| Father/son | 0.405796 |
| Father/daughter | 0.525158 |
| Mother/father | 0.291984 |
| Son/daughter | 0.225282 |

As can be seen from the presented table, the greatest similarity (smaller discrepancy) is found in the pairs "Mother/Son", "Mother/daughter" as compared to "Father/Son" and "Father/daughter", respectively.

Thus, the data obtained show that the microflora of children is inherited mostly from their mother.

Example 2

The Microbiota Nucleus in Samples of Microflora of Various Localization

To confirm the fact that the microorganisms forming the core of the microflora are present in the microflora of various locations, the prevalence of different types of bacteria in the saliva, on the skin and in the feces of the same person was estimated.

The DNA was isolated from the samples (obtained from the mother, see Example 1) using a DNASorb B kit (InterLabService, Russia). Amplification was carried out using universal bacterial primers 27F-534R flanking the hypervariable region of the 16S rRNA gene.

27F: '5-AGAGTTTGATYMTGGCTCAG-3' (SEQ ID NO: 1)

534R: '5-ATTACCGCGGCTGCTGG-3' (SEQ ID NO: 2)

Metagenomic sequencing of the fragment of the 16S rRNA gene was carried out on a Roche-454 Genome Sequencer FLX Ti pyrosequencer.

As a result of the experiment, it was established that the examined samples of saliva, skin, and feces contain representatives of the same taxa of microorganisms, in particular:

Actinomycetales
Bacteroidales
Flavobacteriales
Bacillales
Lactobacillales
Clostridiales
Erysipelotrichales
Selenomonadales
Fusobacteriales
Neisseriales
Campylobacterales
Pasteurellales Thus, it has been established that the "core" of the microflora in the saliva, skin and feces of the same person is represented by bacteria of the same taxa.

According to the data available to the authors, representatives of Archaea are likewise represented in the microbiota.

Example 3

Development of a Pathological Process Under the Effect of Bacteriophages that Are Not Part of the Subject's Own Microflora The experiment was carried out on rats weighing 200 g which consumed enterally with water a complex of bacteriophages selectively acting on the bacteria of the genera *Staphylococcus, Streptococcus, Proteus, Pseudomonas, Salmonella*, and types *E. coli* and *K. pneumonia*, not part of the subject's own microflora, for 10 days. After 10 days of admission, no changes in the functions of the gastrointestinal tract and, in particular, changes in the nature of defecation were recorded in the animals. Simultaneously, after the third day, the animals showed a deterioration in the condition, which manifested itself in a change in the condition of the fur, a decrease in weight, and a general inhibition. After the termination of reception of foreign bacteriophages, the animals were found to have permeability of the intestinal wall, which was detected by an estimation of the change in the ratio of lactulose:mannitol in urine.

The authors used the change in the "lactulose:mannitol" ratio to assess whether unrelated phages cause microflora diseases manifested by the host organism presumably due to the increased intestinal permeability. For this purpose, the changes in urinary excretion of mannitol, lactulose and the lactulose:mannitol ratio in each animal prior to the study and on the 10th day after the use of foreign phages were compared.

On the 10th day, the animals showed a slight (statistically not significant) decrease in mannitol excretion. At the same time, an increase in excretion of lactulose and a sharp increase in the ratio of lactulose:mannitol were registered, which indicates an increase in intestinal permeability (see Table 2).

TABLE 2

| | Mannitol (pmol) | | Lactulose (pmol) | |
|---|---|---|---|---|
| Experimental animal No. | Prior to beginning of the experiment | The 10th day after treatment with foreign bacteriophages | Prior to beginning of the experiment | The 10th day after treatment with foreign bacteriophages |
| 1 | 185 | 173 | 66 | 123 |
| 2 | 164 | 168 | 85 | 193 |
| 3 | 170 | 162 | 82 | 199 |
| 4 | 211 | 205 | 61 | 166 |
| 5 | 157 | 148 | 41 | 133 |
| Average value | 177.4 +/− 21.4 | 171.2 +/− 21.0 | 67 +/− 17.7 | 162.8 +/− 34.3 |

Conclusion from the results of the experiment: The data obtained indicate that oral administration of bacteriophages that are not part of the subject's own microflora can lead to an increase in intestinal permeability, that is, to deterioration of the body condition.

Example 4

Cultivation of the Genuine Microflora Under Conditions that Allow for Growth of the Bacteria Belonging to the Yet Nonculturable Material from the donor was inoculated on a rich nutrient medium. Any suitable nutrient medium can be used as such a nutrient medium. Before inoculation, the material was diluted with sterile water or an isotonic solution of sodium chloride. The samples were incubated at 37° C. The presence of growth (by clouding of the agar mirror), the evaluation of the quantity and quality of various bacteria was carried out after 48 hours of growth. The vast majority of bacteria on the medium grew into mixed communities, similar to individual colonies. As a part of mixed communities, the majority was still nonculturable bacteria, which cannot be cultivated on a nutrient media.

Material from the donor and the conjunction of bacteria cultivated on a rich nutrient medium that provides the growth of the maximum possible number of different foreign microorganisms have been investigated in metagenomic analysis.

As a result of pyrosequencing, a significant species diversity of bacteria was found in sputum, in which 7 microorganisms, 8 series, and 15 species were detected. These microorganisms gave rise on the rich medium used, which indicates its high efficiency for the cultivation of microbes that occur in the donor material.

In the donor's material, when using the test system, the number of sequences was dominated by microorganisms of 2 orders: Pseudomonadales and Burkholderiales. The representation of Pseudomonadales and Burkholderiales in the donor material was 88.3% and 8.5%, and in the test system—76.5% and 1.0%, respectively. The data obtained is summarized in Table 3.

TABLE 3

| Classification | Pathological material (sputum) | Rich nutrient medium |
|---|---|---|
| Order | Bacillales | Bacillales |
| | Pseudomonadales | Pseudomonadales |
| | Clostridiales | Clostridiales |
| | Actinomycetales | Actinomycetales |
| | Lactobacillales | Lactobacillales |
| | Burkholderiales | Burkholderiales |
| Series | Sphingomonadales | Sphingomonadales |
| | Staphylococcaceae | Staphylococcaceae |
| | Corynebacteriaceae | Corynebacteriaceae |
| | Streptococcaceae | Streptococcaceae |
| | Pseudomonadaceae | Pseudomonadaceae |
| | Alcaligenaceae | Alcaligenaceae |
| | Carnobacteriaceae | Carnobacteriaceae |
| | Sphingomonadaceae | Sphingomonadaceae |
| | Oxalobacteraceae | Oxalobacteraceae |
| Species | Staphylococcus epidermidis | Staphylococcus epidermidis |
| | Lactobacillus rhamnosus | Lactobacillus rhamnosus |
| | Pseudomonas sp | Pseudomonas sp |
| | Pseudomonas aeruginosa | Pseudomonas aeruginosa |
| | Achromobacter insolitus | Achromobacter insolitus |

TABLE 3-continued

| Classi-fication | Pathological material (sputum) | Rich nutrient medium |
|---|---|---|
| | Achromobacter xylosoxidans | Achromobacter xylosoxidans |
| | Achromobacter sp | Achromobacter sp |
| | Granulicatella adiacens | Granulicatella adiacens |
| | Sphingomonas sp | Sphingomonas sp |
| | Streptococcus sp | Streptococcus sp |
| | Herbaspirillum sp | Herbaspirillum sp |
| | Corynebacterium striatum | Corynebacterium striatum |
| | Granulicatella adiacens | Granulicatella adiacens |
| | Achromobacter denitrificans | Achromobacter denitrificans |

As a result of the conducted studies, almost 100% coincidence of microorganism species giving growth on a rich nutrient medium was established, in comparison with species in the donor material. The data obtained indicate that the representation of the bacteria cultivated in such manner from the donor material corresponds to the maximum extent to the original composition of the microbiota, and therefore the bacteria thus cultivated can be used for inclusion into a medicament for reconstitution or creation of the microflora.

Example 5

Preparation of the Solution

To prepare the preparation, freshly collected saliva was used in a volume of 5-10 ml, into which flushing from a cotton swab that is used to collect microbes from the buccal mucosa was added. The washing from the swabs was carried out with 1.0 ml of a sterile isotonic sodium chloride solution. As a result, the maximum variety of oral bacteria, which includes cultured and yet nonculturable microbes was obtained. The obtained material was placed in conical tubes, after which rapid precipitation by centrifugation was carried out. To the resulting precipitate, an isotonic sodium chloride solution was added and individual doses comprising 0.001 to 10.0 ml of the original microbial mixture were prepared.

The resulting mixture was stored under various conditions: at a temperature of −70° C., the liquid nitrogen temperature or in the form of a lyophilized dried preparation. Upon freezing, glycerol was added to the mixture as a stabilizer. The samples were stored frozen in separate vials for later use.

Example 6

Restoration of the Normal Microflora After Irradiation

To evaluate the rate of recovery of the microbiota after its damage caused by irradiation, an animal model was used, using bacteria from the microflora of animals that had not been affected as a therapeutic agent.

For this purpose, sexually mature non-linear rats weighing 180-200 grams were used (Rappolpovo nursery, Leningrad region). The animals were kept in pairs until the appearance of offspring. After the age of the offspring reached 4 months, the animals were admitted in the experiment as recipients of the microflora.

Damage to the microflora in rats was caused by combined radiation (18 Gray, day −3) and using a combination of antibiotics: tetracycline, metronidazole 3 days before the start of the experiment (days −3, −2 and −1). On day 0, the animals received an isolated microbial mixture isolated from feces, once (as described in J. Vaahtovuo et al. Quantification of bacteria in human feces using 16S rRNA-hybridization, DNA-staining and flow cytometry. *Journal of Microbiological Methods*, Volume 63, Issue 3, December 2005, Pages 276-286.)

The animals were divided into 5 groups:

Group 1. Recipients of the microflora, which received bacteria of their own microflora, isolated before treatment.

Group 2. Recipients of the microflora, which received the bacteria of the microflora of their own mother.

Group 3. Recipients of the microflora, which received the bacteria of the microflora of their own father.

Group 4. Recipients of the microflora, which received the bacteria of the microflora of unrelated rats.

Group 5. Animals with bacterial infection of microflora, which received as treatment the appropriate volume of the solvent used to prepare the drug (the control group).

The composition of the microflora in the recipients was determined, as described in the previous examples, at the following points in time: before the study, on day 0 (day −3 after damaging the microflora, but before the treatment), 2-4-8-12 weeks after the start of treatment. The degree of microflora recovery was estimated as a percentage of the restoration of the diversity of the phylotypes (expressed in the OTU—operational taxonomic unit) of the microorganisms found in feces.

The results are shown in Table 4

TABLE 4

| | Degree of microflora recovery (OTU, %) | | | | | |
|---|---|---|---|---|---|---|
| Group | before the start of the study | day 0 | 2 weeks | 4 weeks | 8 weeks | 12 weeks |
| 1 | 100 | 26 +/− 3 | 78 +/− 8 | 85 +/− 7 | 93 +/− 3 | 95 +/− 6 |
| 2 | 100 | 26 +/− 3 | 65 +/− 5 | 79 +/− 6 | 87 +/− 4 | 91 +/− 4 |
| 3 | 100 | 26 +/− 3 | 43 +/− 4 | 53 +/− 4 | 62 +/− 3 | 75 +/− 6 |
| 4 | 100 | 26 +/− 3 | 39 +/− 5 | 49 +/− 6 | 56 +/− 5 | 68 +/− 5 |
| 5 | 100 | 26 +/− 3 | 29 +/− 4 | 34 +/− 4 | 43 +/− 5 | 55 +/− 4 |

Thus, the use of representatives of the microbiota of the genuine microflora obtained before the impact on the body of the subject, or representatives of the mother's microbiota can effectively and quickly restore the composition of microflora after the negative impact on the body of the subject leading to impairment or destruction of the subject's own microflora.

Example 7

Restoration of the Normal Microflora After Irradiation

In this example, the authors used an experimental model of impairment of the microflora similar to the one used in the previous example, however, both bacteria and bacteriophages isolated from the microflora of the animals used as a therapeutic solution were not exposed to the impairing effects.

Damage to the microflora in rats was caused by combined radiation (18 Gray, day −3) and using a combination of antibiotics: Tetracycline and metronidazole 3 days before the start of the experiment (days −3, −2 and −1). On day 0, the animals received bacteria and bacteriophages isolated from feces from the debris, once (as described in J. Vaahtovuo et al. Quantification of bacteria in human feces using 16S rRNA-hybridization, DNA-staining and flow cytometry. *Journal of Microbiological Methods*, Volume 63, Issue 3, December 2005, Pages 276-286).

The animals were divided into 5 groups:

Group 1. Recipients of the microflora, which received bacteria and bacteriophages of their own microflora, isolated before treatment.

Group 2. Recipients of the microflora, which received bacteria and bacteriophages of the microflora of their own mother.

Group 3. Recipients of the microflora, which received representatives of their own microflora, isolated before treatment.

Group 4. Recipients of the microflora, which received representatives of the microflora of their own mother.

Group 5. Animals with bacterial infection of microflora, which received as treatment the appropriate volume of the solvent used to prepare the drug (the control group).

The composition of the microflora in the recipients was determined, as described in the previous examples: before the study, on day 0 (day −3 after damaging the microflora, but before the treatment), 2-4-8-12 weeks after the start of treatment. The degree of microflora recovery was estimated as a percentage of the restoration of the diversity of the phylotypes (expressed in the OTU—operational taxonomic unit) of the microorganisms found in feces.

The results are shown in Table 5

TABLE 5

| | Degree of microflora recovery (%) | | | | | |
|---|---|---|---|---|---|---|
| Group | before the start of the study | day 0 | 2 weeks | 4 weeks | 8 weeks | 12 weeks |
| 1 | 100 | 22 +/− 3 | 86 +/− 8 | 96 +/− 5 | 95 +/− 3 | 95 +/− 4 |
| 2 | 100 | 22 +/− 3 | 77 +/− 6 | 92 +/− 4 | 93 +/− 5 | 94 +/− 3 |
| 3 | 100 | 22 +/− 3 | 76 +/− 6 | 83 +/− 6 | 92 +/− 7 | 94 +/− 6 |
| 4 | 100 | 22 +/− 3 | 68 +/− 4 | 77 +/− 5 | 88 +/− 6 | 92 +/− 5 |
| 5 | 100 | 22 +/− 3 | 29 +/− 4 | 34 +/− 4 | 43 +/− 5 | 55 +/− 4 |

Thus, the use of representatives of the microbiota in conjunction with bacteriophages of the genuine microflora obtained before the impact on the body of the subject, or bacteria and bacteriophages of the mother's microbiota can effectively and quickly restore the composition of microflora after the negative impact on the body of the subject.

Example 8

Restoration of the Normal Microflora After its Damage

To evaluate the possibility of restoring the microbiota after its damage, an animal model was used, using bacteriophages from the microflora of the animals as a therapeutic agent, before the formation of the pathological process, or other animals of this brood that were not affected, related on the maternal side.

Damage to microflora in rats was caused by a combination of ampicillin and metronidazole 3 days before the start of the experiment (days −3, −2 and −1). Clinically, the damage to microflora was assessed by the development of the state of dysbiosis, manifested as antibiotic-associated diarrhea, which developed in 20% of the animals by day 0.

On day 0, the animals received (once) bacteriophages obtained from maternally related animals or isolated from the animal prior to damage of the microflora after removing the debris from the faeces, as described in J. Vaahtovuo et al. Quantification of bacteria in human feces using 16S rRNA-hybridization, DNA-staining and flow cytometry. *Journal of Microbiological Methods*, Volume 63, Issue 3, December 2005, pages 276-286. Some animals were administered a combination of bacteria and bacteriophages according to the same procedure.

The animals were divided into 5 groups:

Group 1. Recipients of the microflora, which received bacteriophages of their own microflora, isolated before treatment.

Group 2. Recipients of the microflora, which received bacteriophages of the microflora of their own mother.

Group 3. Recipients of the microflora, which received bacteria and bacteriophages of their own microflora, isolated before treatment.

Group 4. Recipients of the microflora, which received representatives of the microbiota of their own mother and bacteriophages of their mother's microflora.

Group 5. Recipients of the microflora, which received representatives of microbiota of their own microflora, isolated before treatment, without bacteriophages.

Group 6. Animals with bacterial infection of microflora, which received as treatment the appropriate volume of the solvent used to prepare the drug (the control group).

The degree of recovery of microflora was assessed by the number of animals in which the symptoms of dysbacteriosis disappeared and in which defecation normalized.

The results are shown in Table 6.

TABLE 6

| | Number of animals in the group/number of animals with symptoms of dysbiosis | | | |
|---|---|---|---|---|
| Group | day 0 | day 3 | day 5 | day 7 |
| 1 | 8/8 | 8/2 | 8/0 | 8/0 |
| 2 | 8/8 | 8/2 | 8/0 | 8/0 |
| 3 | 8/8 | 8/2 | 8/0 | 8/0 |
| 4 | 8/8 | 8/2 | 8/0 | 8/0 |
| 5 | 8/8 | 8/4 | 8/2 | 8/0 |
| 6 | 8/8 | 8/8 | 8/7 | 8/6 |

Thus, the use of representatives of bacteriophages obtained from the genuine microflora before the impact on the body of the subject, or bacteriophages obtained from their mother's microflora can effectively and quickly restore the composition of microflora after the negative impact. The use of bacteriophages in conjunction with the microbiota is more effective than the use of bacteria alone.

Example 9

Influence of the Mother's Microflora on the Restoration of Microflora of the Offspring Delivered by Caesarean Section To assess the influence of the mother's microflora on the restoration of microflora of the offspring delivered by Caesarean section, a model with white non-linear rats was used. It is known that offspring delivered by Caesarean section show a slow increase in weight in comparison with the offspring born naturally. For this purpose, pregnancy of some of the rats of the test group was resolved by Caesarean section, under anesthesia, in accordance with the declaration of the Guide for the Care and Use of Laboratory (Institute of Laboratory Animal Resources (US). Committee on Care, Use of Laboratory Animals, & National Institutes of Health (US). Division of Research Resources. (1985). *Guide for the care and use of laboratory animals*. National Academies.).

Progeny from each female was divided into the following groups:

Experimental group—received a mixture of bacteria and phages, previously isolated from the mother's feces in the form of drops on a daily basis.

Control group—received only their mother's milk.

The dynamics of weight gain was estimated in % of the norm on days 7 and 14 after delivery (Table 7).

TABLE 7

| Group | Weight gain in % of the norm | |
| --- | --- | --- |
| | day 7 | day 14 |
| Experimental group | 78 +/− 5 | 75 +/− 6 |
| Control group | 96 +/− 4 | 102 +/− 5 |

It was established that administration of bacteria and bacteriophages from the mother's microflora to the animals delivered by cesarean section leads to normalization of the weight gain in the animals.

Example 10

Assessment of the Possibility of Additional Cultivation of Microbiota Representatives After Storage for Enrichment of the Preparation.

Using rich nutrient media, microorganisms were cultivated that included bacteria isolated from the genuine microbiota. Any nutrient medium suitable for cultivation of microorganisms can be used as a nutrient medium. A comparative metagenomic study was carried out with a qualitative determination of representation of the microorganism in the initial material and cultivated on the nutrient medium used. The possibility of preserving the representation of the microorganisms after prolonged storage (12 months at −70° C.) was also evaluated.

Isolation of DNA from pathological material and bacteria cultivated on the medium was carried out using a standard set of "Sorb-B DNA" (Russia) according to the available protocol. Amplification was carried out using eubacterial primers 27F-534R flanking the hypervariable region of the 16S rRNA gene.

27F: '5-AGAGTTTGATYMTGGCTCAG-3' (SEQ ID NO: 3)

534R: '5-ATTACCGCGGCTGCTGG-3' (SEQ ID NO: 4)

Metagenomic sequencing of the fragment of the 16S rRNA gene was carried out on a Roche/454 Genome Sequencer FLX Titanium pyrosequencer. Each sequence obtained during pyrosequencing was identified by comparison with the sequences of GenBank and EzTaxon databases using the BLASTN search algorithms and by pairwise comparison.

For identification, the following similarity thresholds were used (x=similarity): species (x>97%), genera (97>x≥94%), series (94>x≥90%), orders (90>x≥85%), classes (85>x≥80%), fillets (80>x≥75%). To determine the species diversity, taxonomic composition and comparison of communities, Pyrosequencing pipeline software program (http://pyro.cme.msu.edu) was used. The resulting sequences were aligned and cluster analysis was carried out using the Complete Linkage Clustering program, which is part of Pyrosequencing pipeline. Classification of species at all stages of the work is based on the genotypic approach in accordance with the international code of the nomenclature of bacteria (ICNB). In case the representative sequence had homology with the validated microorganism sequence of over 97%, the cluster was assigned to the corresponding species.

As a result of pyrosequencing, a significant species diversity of microorganisms was found in saliva, in the composition of which 7 microorganisms, 8 series, and 15 species were detected. The same microorganisms gave rise to the nutrient medium developed by the authors, which indicates its high efficiency for ensuring the growth of the whole variety of microbes.

TABLE 8

| Microbiota derived from saliva | Microorganisms cultivated on a nutrient medium | Microorganisms cultivated on a nutrient medium after 12 months of storage |
| --- | --- | --- |
| Actinomycetaceae | Actinomycetaceae | Actinomycetaceae |
| Micrococcaceae | Micrococcaceae | Micrococcaceae |
| Coriobacteriaceae | Coriobacteriaceae | Coriobacteriaceae |
| Porphyromonadaceae | Porphyromonadaceae | Porphyromonadaceae |
| Prevotellaceae | Prevotellaceae | Prevotellaceae |
| Flavobacteriaceae | Flavobacteriaceae | Flavobacteriaceae |
| Bacillales | Bacillales | Bacillales |
| Carnobacteriaceae | Carnobacteriaceae | Carnobacteriaceae |
| Streptococcaceae | Streptococcaceae | Streptococcaceae |
| Eubacteriaceae | Eubacteriaceae | Eubacteriaceae |
| Lachnospiraceae | Lachnospiraceae | Lachnospiraceae |
| Peptostreptococcaceae | Peptostreptococcaceae | Peptostreptococcaceae |
| Ruminococcaceae | Ruminococcaceae | Ruminococcaceae |
| Erysipelotrichaceae | Erysipelotrichaceae | Erysipelotrichaceae |
| Veillonellaceae | Veillonellaceae | Veillonellaceae |
| Fusobacteriaceae | Fusobacteriaceae | Fusobacteriaceae |
| Leptotrichiaceae | Leptotrichiaceae | Leptotrichiaceae |
| Burkholderiaceae | Burkholderiaceae | Burkholderiaceae |
| Neisseriaceae | Neisseriaceae | Neisseriaceae |
| Campylobacteraceae | Campylobacteraceae | Campylobacteraceae |
| Pasteurellaceae | Pasteurellaceae | Pasteurellaceae |
| Pseudomonadaceae | Pseudomonadaceae | Pseudomonadaceae |
| Bacillaceae | Bacillaceae | Bacillaceae |
| Aerococcaceae | Aerococcaceae | Aerococcaceae |
| Clostridiales | Clostridiales | Clostridiales |

As a result of the conducted studies, 100% coincidence of the types of microorganisms that give growth on the developed nutrient medium was established, both immediately after collection of the material, and after 12 months of storage.

Example 11

Life Span Assessment

The change in the life span of experimental animals was evaluated, while both bacteria with bacteriophages and bacteriophages obtained from the microflora of the same animals, or previously obtained from relatives on the maternal side at a young age, were used as a therapeutic solution.

Starting from the 10$^{th}$ months of age, the animals received bacteria and bacteriophages isolated from feces after removing of debris, once (as described in J. Vaahtovuo et al. Quantification of bacteria in human feces using 16S rRNA-hybridization, DNA-staining and flow cytometry. *Journal of Microbiological Methods*, Volume 63, Issue 3, December 2005, Pages 276-286.

The animals (white non-linear mice) were divided into 5 groups:

Group 1. Recipients of the microflora, which received bacteria and bacteriophages isolated from their own microflora at a young age.

Group 2. Recipients of the microflora, which received bacteria and bacteriophages isolated from their own mother's microflora at a young age.

Group 3. Recipients of the microflora, which received bacteriophages isolated from their own microflora at a young age.

Group 4. Recipients of the microflora, which received bacteriophages isolated from their own mother's microflora at a young age.

Group 5. Animals, which received as treatment the appropriate volume of the solvent used to prepare the solution (the control group).

The results are shown in Table 9.

TABLE 9

| Group | Increase in life expectancy |
|---|---|
| 1 | +38% |
| 2 | +26% |
| 3 | +28% |
| 4 | +21% |
| 5 | 0% |

Thus, the use of microorganisms isolated from the genuine microbiota or microflora of relatives on the maternal side, together with bacteriophages obtained from their own microflora or microflora of relatives on the maternal side, and also the use of only isolated bacteriophages obtained at a young age from the animal itself or from its relatives on the maternal side, allows to effectively and quickly restore the composition of microflora after a negative impact, which, in turn, contributes to an increase in life expectancy, as can be seen from the data shown in Table 9.

Example 12

Evaluation of Correction of Increased Intestinal Permeability

The possibility of correcting the increase in intestinal permeability was evaluated; while both bacteria with bacteriophages and bacteriophages previously obtained from the microflora of the same animals, or obtained from relatives on the maternal side at a young age, were used as a therapeutic solution. Increased intestinal permeability, or the "leaky gut syndrome" syndrome, is associated with development of a significant number of pathologies: Crohn's disease, irritable bowel syndrome, rheumatoid arthritis, Alzheimer's disease, Parkinson's disease, schizophrenia, depression, autism, bipolar disorder, arrhythmias, cachexia, sudden death syndrome, renal and hepatic insufficiency, glomerulonephritis and others.

To simulate the increase in intestinal permeability, winstar rats were given 4 ml of 40% ethanol at a rate of 2 g/kg/day. This dose was progressively increased in such a way that by the 14th day the animals received 8 g/kg/day of 40% ethanol. After 30 days, the animals were divided into 5 groups:

Group 1. Recipients of the microflora, which received bacteria and bacteriophages of their own microflora, isolated before alcohol administration.

Group 2. Recipients of the microflora, which received bacteria and bacteriophages of their own mother's microflora, isolated before alcohol administration.

Group 3. Recipients of the microflora, which received bacteriophages of their own microflora, isolated before alcohol administration.

Group 4. Recipients of the microflora, which received bacteriophages of their own mother's microflora, isolated before alcohol administration.

Group 5. Animals, which received as treatment the appropriate volume of the solvent used to prepare the solution (the control group).

Group 6. Animals of the same brood that did not receive ethanol (with a constant intestinal permeability rate).

After 10 days of treatment, changes in intestinal permeability were determined in animals based on a lactulose/mannitol test.

The results are shown in Table 10.

TABLE 10

| Group | Lactulose/mannitol ratio on the first day of testing before the alcohol administration | Lactulose/mannitol ratio on day 30 after the alcohol administration | Lactulose/mannitol ratio 10 days after the start of treatment |
|---|---|---|---|
| 1 | 0.27 ± 0.05 | 1.28 ± 0.07 | 0.35 ± 0.08 |
| 2 | 0.42 ± 0.02 | 0.94 ± 0.06 | 0.48 ± 0.05 |
| 3 | 0.31 ± 0.03 | 1.02 ± 0.03 | 0.39 ± 0.04 |
| 4 | 0.43 ± 0.06 | 0.96 ± 0.08 | 0.51 ± 0.07 |
| 5 | 0.29 ± 0.05 | 1.19 ± 0.22 | 1.23 ± 0.05 |
| 6 | 0.30 ± 0.04 | 0.90 ± 0.07 | 0.26 ± 0.05 |

Thus, the use of microbiota in conjunction with the bacteriophages of the genuine microflora or the microflora of relatives on the maternal side, as well as only isolated bacteriophages obtained before induction of an increase in the gut permeability, in the animal itself or in its relatives on the maternal side, allows for effective and quick correction of leaky gut syndrome and restoration of intestinal permeability.

Example 13

Preventing Development of Tumor Processes

The possibility of preventing the appearance of a tumor process in experimental animals using the solution of the present invention was evaluated, with both bacteria with bacteriophages and bacteriophages previously obtained from the microflora of the same animals, or obtained from relatives on the maternal side at a young age, used as a therapeutic solution.

Starting at week 8, azoxymethane was injected intraperitoneally at the rate of 10 mg/kg once in a week for 6 weeks, in order to induce carcinogenesis, as described in Fukutake M et al. Suppressive effects of nimesulide, a selective inhibitor of cyclooxygenase-2, on azoxymethane-induced colon carcinogenesis in mice. *Carcinogenesis*, Volume 19, Issue 3, 1998, Pages 1939-1942.

Starting from day 1 of azoxymethane administration, the animals received as a therapeutic solution both bacteria with bacteriophages and bacteriophages previously obtained from the microflora of the same animals, or obtained from their relatives on the maternal side at a young age.

The animals (white non-linear mice) were divided into 5 groups:

Group 1. Recipients of the microflora, which received bacteria and bacteriophages isolated from their own microflora at a young age.

Group 2. Recipients of the microflora, which received bacteria and bacteriophages isolated from their own mother's microflora at a young age.

Group 3. Recipients of the microflora, which received bacteriophages isolated from their own microflora at a young age.

Group 4. Recipients of the microflora, which received bacteriophages isolated from their own mother's microflora at a young age.

Group 5. Animals, which received as treatment the appropriate volume of the solvent used to prepare the solution (the control group).

The results are shown in Table 11.

TABLE 11

| Group | Number of mice with developed intestinal carcinoma/ total number of animals in the group (%) |
|---|---|
| 1 | 0/10 (0%) |
| 2 | 2/10 (20%) |
| 3 | 3/10 (30%) |
| 4 | 3/10 (30%) |
| 5 | 6/10 (60%) |

Thus, from the data given in Table 11, it can be seen that the use of microorganisms isolated from the genuine microbiota or microflora of relatives on the maternal side, together with bacteriophages obtained from their own microflora or microflora of relatives on the maternal side, and also the use of only isolated bacteriophages obtained at a young age from the animal itself or from its relatives on the maternal side, allows to reduce the likelihood of carcinogenesis development.

Example 14

Treatment of Tumor Processes

The change in the development of a tumor process in experimental animals using the solution of the present invention was evaluated, with both bacteria with bacteriophages and bacteriophages previously obtained from the microflora of the same animals, or obtained from relatives on the maternal side at a young age, used as a therapeutic solution.

Starting at week 8, azoxymethane was injected intraperitoneally at the rate of 10 mg/kg once in a week for 6 weeks, in order to induce carcinogenesis, as described in Fukutake M et al. Suppressive effects of nimesulide, a selective inhibitor of cyclooxygenase-2, on azoxymethane-induced colon carcinogenesis in mice. *Carcinogenesis*, Volume 19, Issue 3, 1998, Pages 1939-1942.

Seven days after the completion of azoxymethane administration, with positive tumor induction were selected and for the following 4 weeks the animals received both bacteria with bacteriophages and bacteriophages previously obtained from the microflora of the same animals, or obtained from their relatives on the maternal side at a young age, as a therapeutic agent. The change in tumor size progression was assessed.

The animals (white non-linear mice) were divided into 5 groups:

Group 1. Recipients of the microflora, which received bacteria and bacteriophages isolated from their own microflora at a young age.

Group 2. Recipients of the microflora, which received bacteria and bacteriophages isolated from their own mother's microflora at a young age.

Group 3. Recipients of the microflora, which received bacteriophages isolated from their own microflora at a young age.

Group 4. Recipients of the microflora, which received bacteriophages isolated from their own mother's microflora at a young age.

Group 5. Animals, which received as treatment the appropriate volume of the solvent used to prepare the solution (the control group).

The results are shown in Table 12.

TABLE 12

| Group | Tumor size before treatment ($mm^3$) | Tumor size after 4 weeks of treatment ($mm^3$) (% change) |
|---|---|---|
| 1 | 22.4 ± 4.5 | 23.5 ± 5.2 (+4.9%) |
| 2 | 22.4 ± 4.5 | 25.7 ± 6.3 (+14%) |
| 3 | 22.4 ± 4.5 | 28.5 ± 6.8 (+27.2%) |
| 4 | 22.4 ± 4.5 | 30.4 ± 7.1 (+35.7%) |
| 5 | 22.4 ± 4.5 | 160.3 ± 28.7 (+715%) |

Thus, from the data given in Table 12, it can be seen that the use of microorganisms isolated from the genuine microbiota or microflora of relatives on the maternal side, together with bacteriophages obtained from the genuine microflora or microflora of relatives on the maternal side, and also the use of only isolated bacteriophages obtained at a young age from the animal itself or from its relatives on the maternal side, allows to inhibit carcinogenesis development.

The present application describes a number of examples and embodiments of the invention. Nevertheless, it must be borne in mind that various modifications of the described examples and embodiments can be developed, while not departing from the scope and the essence of the invention in principle. With this in mind, other embodiments are included in the scope of the items listed below. At that, all the numerical ranges described herein include all the sub ranges contained therein, as well as any individual values within the scope of these ranges. All publications, patents and patent applications mentioned in this description are hereby incorporated by reference.

The invention claimed is:

1. A pharmaceutical dosage form for restoration or creation of microbiota of a subject, comprising (i) an active component comprising bacteria and bacteriophages isolated from microbiota of the subject or microbiota of a donor selected from the subject's mother, subject's sisters and brothers of the whole blood, and other relatives on the maternal side, and (ii) a pharmaceutically acceptable excipient.

2. The pharmaceutical dosage form according to claim 1, wherein the dosage form comprises at least one bacterium selected from bacteria belonging to: Actinomycetales, Bacteroidales, Flavobacteriales, Bacillales, Lactobacillales, Clostridiales, Erysipelotrichales, Selenomonadales, Fusobacteriales, Neisseriales, Campylobacterales, and Pasteurellales.

3. The pharmaceutical dosage form according to claim 1, wherein the dosage form comprises at least one bacterium selected from bacteria belonging to: Aerococcaceae, Burkholderiaceae, Carnobacteriaceae, Coriobacteriaceae, Erysipelotrichaceae, Eubacteriaceae, Lachnospiraceae, Leptotrichiaceae, Micrococcaceae, Peptostreptococcaceae, Porphyromonadaceae, Prevotellaceae, Pseudomonadaceae, Ruminococcaceae, Streptococcaceae, and Veillonellaceae.

4. The pharmaceutical dosage form according to claim 1, wherein the dosage form comprises Archaea and/or fungi isolated from microbiota of the subject or microbiota of a donor selected from the subject's mother, subject's sisters and brothers of the whole blood, and other relatives on the maternal side.

5. A pharmaceutical dosage form for restoration or creation of microbiota of a subject, comprising (i) an active component comprising bacteriophages isolated from microbiota of the subject, or microbiota of a donor selected from the subject's mother, subject's sisters and brothers of the whole blood, and other relatives on the maternal side, and (ii) a pharmaceutically acceptable excipient.

6. The pharmaceutical dosage form according to claim 5, wherein the active component comprises bacteriophages isolated from microbiota of a donor selected from the subject's sisters and brothers of the whole blood, and other relatives on the maternal side.

7. The pharmaceutical dosage form according to claim 1, wherein the ratio of bacteriophages to the bacteria is 1000:1 to 100:1.

8. The pharmaceutical dosage form according to claim 1, wherein the active component comprises bacteria and/or bacteriophages cultivated on a nutrient medium.

9. The pharmaceutical dosage form according to claim 1, wherein the pharmaceutically acceptable excipient is selected from isotonic sodium chloride, activated carbon, silica, chalk, sugar, lactose, gelatin, starch, polyvinyl alcohol (PVA), polyvinylpyrrolidone (PVP), cellulose, methyl cellulose (MC), hydroxypropylmethyl cellulose (CMO), carboxymethyl cellulose (CMC), and sodium carboxymethylcellulose (Na-CMC).

10. The pharmaceutical dosage form according to claim 1, wherein the active component is obtained by cultivation of at least a portion of bacteria and/or bacteriophages isolated from microbiota of the subject or microbiota of the donor under aerobic and/or anaerobic conditions.

11. The pharmaceutical dosage form according to claim 10, wherein the active component is obtained by cultivation of $10^9$ to $10^{12}$ bacteria per ml.

12. The pharmaceutical dosage form according to claim 1, wherein the active component comprises bacteria and bacteriophages isolated from the microbiota of saliva, mucous membranes, skin, gastrointestinal tract, and/or feces.

13. The pharmaceutical dosage form according to claim 1, wherein the active component is formulated in a form suitable for freezing and long-term storage.

14. The pharmaceutical dosage form according to claim 1, wherein the dosage form further comprises bacteria that enhance the ability of bacteria in the active component to colonize certain areas of the skin or mucosa.

15. The pharmaceutical dosage form according to claim 1, wherein the dosage form is prepared in the form of capsules, tablets, pellets, caplets, powder, aerosol, lyophilizate, gel, suspension cream, emulsion, or suspension in a nutrient medium or other suitable liquid.

16. The pharmaceutical dosage form according to claim 1, wherein the dosage form is formulated in a form selected from the forms suitable for dissolution in the oral cavity, small intestine, stomach, and large intestine.

17. The pharmaceutical dosage form according to claim 1, wherein the dosage form is prepared in a form suitable for buccal or sublingual administration.

18. The pharmaceutical dosage form according to claim 1, wherein the dosage form is prepared in a form suitable for transmucosal administration.

19. The pharmaceutical dosage form according to claim 1, wherein the dosage form is prepared in a form suitable for intravaginal administration.

20. The pharmaceutical dosage form according to claim 1, wherein the active component comprises bacteria and bacteriophages isolated from the microbiota of a donor selected from subject's sisters and brothers of the whole blood and other relatives on the maternal side.

21. The pharmaceutical dosage form of claim 1, wherein the dosage form comprises $10^3$ to $10^{12}$ bacteriophages per 1 ml of the dosage form.

22. The pharmaceutical dosage form of claim 6, wherein the dosage form comprises $10^3$ to $10^{12}$ bacteriophages per 1 ml of the dosage form.

23. A method for the treatment of a disease in a subject in need thereof, comprising administering to the subject the dosage form according to claim 1, wherein the disease is selected from ulcerative colitis, irritable bowel syndrome, increased intestinal permeability, intestinal permeability syndrome, mucosal candidiasis, bowel dysfunction, flatulence, vaginosis, tumor diseases, Crohn's disease, rheumatoid arthritis, Alzheimer's disease, Parkinson's disease, schizophrenia, depression, autism, bipolar disorder, arrhythmias, cachexia, aging, sudden death syndrome, renal insufficiency, hepatic insufficiency, and glomerulonephritis.

24. A method for creating a normal microbiota in a baby delivered by Caesarean section, comprising administering to the baby the dosage form according to claim 1, wherein the active component of the dosage form comprises bacteria and bacteriophages isolated from the baby's mother's microbiota or the microbiota of a donor selected from the baby's sisters and brothers of the whole blood and other relatives on the maternal side.

25. A method for creating a normal microbiota in a baby delivered by a surrogate mother, comprising administering to the baby the dosage form according to claim 1, wherein the active component of the dosage form comprises bacteria and bacteriophages isolated from the baby's genetic mother's microbiota or the microbiota selected from the baby's sisters and brothers of the whole blood and other relatives on the maternal side.

26. A method for prevention and/or treatment of a tumor disease in a subject in need thereof, comprising administering to the subject the dosage form according to claim 1.

27. A method for treatment of increased intestinal permeability in a subject in need thereof, comprising administering to the subject the dosage form according to claim 1.

28. The method according to claim 23, wherein the active component of the dosage form comprises bacteria and/or bacteriophages cultivated on a nutrient medium and wherein said bacteria and/or bacteriophages are added to the active component 1 hour to 1 day before the administration of the dosage form.

29. The method according to claim 24, wherein the active component of the dosage form comprises bacteria and/or bacteriophages cultivated on a nutrient medium and wherein said bacteria and/or bacteriophages are added to the active component 1 hour to 1 day before the administration of the dosage form.

30. The method according to claim 25, wherein the active component of the dosage form comprises bacteria and/or bacteriophages cultivated on a nutrient medium and wherein said bacteria and/or bacteriophages are added to the active component 1 hour to 1 day before the administration of the dosage form.

31. The method according to claim 26, wherein the active component of the dosage form comprises bacteria and/or bacteriophages cultivated on a nutrient medium and wherein said bacteria and/or bacteriophages are added to the active component 1 hour to 1 day before the administration of the dosage form.

32. The method according to claim 27, wherein the active component of the dosage form comprises bacteria and/or bacteriophages cultivated on a nutrient medium and wherein said bacteria and/or bacteriophages are added to the active component 1 hour to 1 day before the administration of the dosage form.

* * * * *